United States Patent
Giordano et al.

(10) Patent No.: US 10,720,232 B2
(45) Date of Patent: Jul. 21, 2020

(54) DISTRIBUTED HEALTHCARE RECORDS MANAGEMENT

(71) Applicant: Accenture Global Solutions Limited, Dublin (IE)

(72) Inventors: Giuseppe Giordano, Juan les Pins (FR); Emmanuel Viale, Cagnes sur Mer (FR); Luca Schiatti, Juan les Pins (FR); Hugo Borne-Pons, Val-de-Marne (FR)

(73) Assignee: Accenture Global Solutions Limited, Dublin (IE)

(*) Notice: Subject to any disclaimer, the term of this patent is extended or adjusted under 35 U.S.C. 154(b) by 1117 days.

(21) Appl. No.: 15/098,098

(22) Filed: Apr. 13, 2016

(65) Prior Publication Data

US 2017/0300627 A1 Oct. 19, 2017

(51) Int. Cl.
*G16H 10/60* (2018.01)
*H04L 29/08* (2006.01)
(Continued)

(52) U.S. Cl.
CPC ......... *G16H 10/60* (2018.01); *G06F 21/6245* (2013.01); *G06F 21/645* (2013.01);
(Continued)

(58) Field of Classification Search
None
See application file for complete search history.

(56) References Cited

U.S. PATENT DOCUMENTS

2002/0194024 A1  12/2002  Kleinschmidt
2009/0019516 A1* 1/2009  Hammoutene ..... G06F 21/6245
726/1
(Continued)

FOREIGN PATENT DOCUMENTS

WO  WO 2001/013274  2/2001

OTHER PUBLICATIONS

Tori Adams, "Blockchain, Smart Contracts, and Health: Booz Allen Hamilton and the Blockchain Revolution", Dec. 11, 2015, [retrieved on Jun. 29, 2017 and Sep. 3, 2019], Retrved from the Internet:URL<https://www.linkedin.com/pulse/blockchain-smart-contracts-health-booz-allen-hamilton-tori-adams>, 18 pgs (Year: 2015).*
(Continued)

*Primary Examiner* — Steven S Kim
*Assistant Examiner* — Jason B Fenstermacher
(74) *Attorney, Agent, or Firm* — Fish & Richardson P.C.

(57) ABSTRACT

This document describes systems, methods, devices, and other techniques for managing healthcare records. In some implementations, a computing system is provided that includes an electronic ledger, a first program module, and a second program module. The electronic ledger can store entries of medical record management events invoked by participants in a distributed computing network. The first program module can be assigned to an account of a first user on the distributed computing network and can identify (i) medical records of the first user and (ii) accounts of users other than the first user that are authorized to access the medical records of the first user. The second program module can be assigned to an account of a second user on the distributed computing network and can call the first program module to request access to a set of one or more of the medical records of the first user.

22 Claims, 9 Drawing Sheets

(51) Int. Cl.
*G06F 21/64* (2013.01)
*G16H 40/67* (2018.01)
*G06F 21/62* (2013.01)
*H04L 29/06* (2006.01)

(52) U.S. Cl.
CPC .......... *G16H 40/67* (2018.01); *H04L 63/102* (2013.01); *H04L 67/104* (2013.01)

(56) References Cited

U.S. PATENT DOCUMENTS

| | | | |
|---|---|---|---|
| 2015/0332283 A1* | 11/2015 | Witchey | G06Q 30/018 705/3 |
| 2016/0027229 A1 | 1/2016 | Spanos et al. | |
| 2017/0287068 A1* | 10/2017 | Nugent | G06Q 20/08 |

OTHER PUBLICATIONS

Melanie Swan: "Blockchain: Blueprint for a New Economy", Jan. 22, 2015, O'Reilly, ISBN: 978-1-4919-2049-7 (Year: 2015).*
Australian Office Action for Application No. 2017202356, dated Aug. 2, 2017, 6 pages.
European Extended Search Report for Application No. 17166092.1, dated Sep. 22, 2017, 19 pages.
Tori Adams, "Blockchain, Smart Contracts, and Health: Booz Allen Hamilton and the Blockchain Revolution", Dec. 11, 2015, [retrieved on Jun. 29, 2017], Retrieved from the Internet: URL<https://www.linkedin.com/pulse/blockchain-smart-contracts-health-booz-allen-hamilton-tori-adams>, 7 pages.
Liberty.me: "The Tatiana Show—Ryan Singer of Blockchain Health & David Johnson of Factom", youtube, Mar. 15, 2016, [retrieved on July 11, 2017], Retrieved from the Internet: URL<http://www.youtube.com/watch?v=UnRVFsyansc>, & Ryan Singer et al., "I Don't Want You to Have My Data Anymore", Mar. 30, 2016, [retrieved on Jun. 30, 2017], Retrieved from the Internet: URL: <http://www.americanbanker.com/video/i-dont-want-you-to-have-my-data-anymore>, 1 page.
Melanie Swan: "Blockchain: Blueprint for a New Economy," O'Reilly, Chapters 1-7, Jan. 24, 2015, 142 pages.
'web.archive.org' [online]. "Block chain (database)—Wikipedia, the free encyclopedia", Mar. 30, 2016, [retrieved on 2017-09-2013], Retrieved from the Internet: <https://web.archive.org/web/20160330201409/https://en.wikipedia.org/wiki/block_chain (database)>, 6 pages.
Fintech et al., "Making sense of bitcoin and blockchain: PwC," Feb. 1, 2016, [retrieved on Feb. 1, 2016], Retrieved from the Internet, URL: <https://www.pwc.com/us/en/financial-services/fintech/bitcoin-blockchain-cryptocurrency.html>, 4 pages.

Peter B. Nichol: "Blockchain Technology: The Solution for Healthcare Interoperability," Linkedin, Nov. 19, 2015, [retrieved on Jul. 10, 2017], Retrieved from the Internet: URL: <https://www.linkedin.com/pulse/blockchain-technology-solution-heathcare-peter-b-nichol>, 5 pages.
Australian Office Action in Australian Application No. 2017202356, dated Dec. 12, 2017, 2 pages.
'www.ethereum.org' [online]. "The Greeter: Building a smart contract using the command line," Jan. 26, 2017, [retrieved from the internet] URL <https://web.archive.org/web/20170126065238/https://ethereum.org/greeter> 13 pages.
'www.github.com' [online]. "Home: Jeffrey Wilcke" May 6, 2016, [retrieved from the internet] URL<https://github.com/ethereum/go-ethereum/wiki> 2 pages.
'www.github.com' [online]. "White Paper: Bitspill," Mar. 22, 2016, [retrieved from the internet] URL<https://github.com/ethereum/wiki/wiki/White-Paper/c764c61485ea9830fd2cc70e6435dda7058699aa> 22 pages.
'en.bitcoin.it' [online]. "Contract," Oct. 22, 2015, [retrieved from the internet] URL<https://en.bitcoin.it/w/index.php?title=Contract&oldid=59172> 13 pages.
'github.com' [online]. "Managing Your Accounts: Viktor Trón," Jul. 25, 2015, [retrieved from the internet] URL<https://github.com/ethereum/go-ethereum/wiki/Managing-your-accounts/b676a0327c9c864b55129073516dff43ddle1373> 6 pages.
Melanie Swan, "Blockchain: Blueprint for a New Economy," O'Reilly 2015, 149 pages.
Linn et al., "Blockchain For Health Data and Its Potential Use in Health IT and Health Care Related Research," Feb. 7, 2017, 10 pages.
'healthstandards com' [online]. "Rewriting Healthcare on the Blockchain: Leonard Kish," Jul. 16, 2014, [retrieved from the internet]URL<https://healthstandards.com/blog/2014/07/16/blockchain/> 6 pages.
Anonymous: "Smart contract—Wikipedia",Apr. 5, 2016, [retrieved-on Apr. 8, 2019], Retrieved from the Internet: URL:https://en.wikipedia.org/w/index.php?title=Smart contract&oldid=713713186.
EP Extended Search Report in European Appln. No. EP18214054, dated Apr. 10, 2019, 15 pages.
Melanie Swan: "Bloackchain Health" Feb. 8, 2015, O'Reilly, pp. 59-61.
Melanie Swan: "Chapter 2: Blockchain 2.0:Contracts" Feb. 8, 2015, O'Reilly, pp. 9-26.
Sanjay Panikkar: 11 ADEPT: An IoT Practitioner Perspective Draft Copy for Advance Review II. Key Objectives for Proof of Concept, Jan. 7, 2015 Retrieved from the Internet: URL:https://ia802601.us.archive.org/4/items/pdfy-esMcC00dKmdo53- /IBM ADEPT.

\* cited by examiner

*Accessing a Medical Record*

*Fraud Detection Capabilities*

```
                    800─┐
                        ↓

┌─────────────────────────────────────────────┐
    │ Identify a command from a first user to access a │
    │ medical record of a patient having an account on a │
    │     distributed computing network           │
    │                                         802 │
    └─────────────────────────────────────────────┘
                        ↓
    ┌─────────────────────────────────────────────┐
    │ Call first smart contract assigned to first user to │
    │  invoke access event in response to command │
    │                                         804 │
    └─────────────────────────────────────────────┘
                        ↓
    ┌─────────────────────────────────────────────┐
    │  Generate, with first smart contract, request to │
    │     access the medical record of the patient │
    │                                         806 │
    └─────────────────────────────────────────────┘
                        ↓
    ┌─────────────────────────────────────────────┐
    │       Check rights of first user and patient │
    │                                         808 │
    └─────────────────────────────────────────────┘
                        ↓
    ┌─────────────────────────────────────────────┐
    │ Provide request to access medical record of patient │
    │   to a second smart contract assigned to patient │
    │                                         810 │
    └─────────────────────────────────────────────┘
                        ↓
    ┌─────────────────────────────────────────────┐
    │  Use second smart contract to provide, to the first │
    │    user, access to the patient's medical record │
    │                                         812 │
    └─────────────────────────────────────────────┘
                        ↓
    ┌─────────────────────────────────────────────┐
    │       Broadcast event to network, add to ledger │
    │                                         814 │
    └─────────────────────────────────────────────┘
                        ↓
    ┌─────────────────────────────────────────────┐
    │         Obtain medical record of first patient │
    │                                         816 │
    └─────────────────────────────────────────────┘
```

FIG. 8

DISTRIBUTED HEALTHCARE RECORDS MANAGEMENT

TECHNICAL FIELD

This document generally relates to secure file storage and distribution in a decentralized computing network. Some implementations include a distributed electronic medical records system.

BACKGROUND

Electronic medical record systems can facilitate storage and management of patient medical data and other forms of electronic medical records. Electronic medical record systems are sometimes operated privately by individual healthcare organizations. As an example, a hospital, a small physicians' practice group, and a pharmacy may each operate separate electronic medical record systems for their respective uses. Recently, some healthcare organizations have transitioned from paper-based medical record systems to electronic medical records as a long-term cost-savings measure, to comply with government regulations and incentives, to reduce paper clutter, and to provide improved patient services.

SUMMARY

This document generally describes systems, methods, devices, and other techniques for implementing a medical records management system in a decentralized computing network that provides a distributed ledger. In some implementations, a collection of computing systems in a decentralized network may separately store and maintain full copies of the distributed ledger. The ledger may include blocks of transactions that indicate actions that have been taken on the network since its genesis. In some implementations, the ledger also stores program modules, referred to as smart contracts, which allow participants in a distributed medical records management network to interact with the ledger and with each other. For example, doctors, patients, pharmacists, and insurers may be issued role-specific smart contracts that allow the participants to invoke various records management events on the network. A doctor, for instance, may use his or her smart contract to add or retrieve a medical record from a patient. Conversely, a patient's smart contract may identify a collection of medical records owned by the patient that reflect the patient's medical history or medical profile. The patient's smart contract may comprise code that, when executed, sends data to an authorized user's smart contract (e.g., the smart contract of a patient's attending physician) that allows the authorized user to access the patient's medical records.

Some implementations of the subject matter described herein include a computing system having an electronic ledger, a first program module, and a second program module. The electronic ledger can store entries of medical record management events invoked by participants in a distributed computing network, wherein respective instances of the electronic ledger are stored at each of a plurality of nodes in the distributed computing network. The first program module can be assigned to an account of a first user on the distributed computing network and can include executable code that is arranged to identify (i) medical records of the first user and (ii) accounts of users other than the first user that are authorized to access the medical records of the first user. The second program module can be assigned to an account of a second user on the distributed computing network and can include executable code that is arranged to call the first program module to request access to a set of one or more of the medical records of the first user, wherein the first program module is arranged to make the set of medical records of the first user available to the account of the second user in response to determining that the account of the second user is authorized to access the set of medical records.

These and other implementations can optionally include one or more of the following features.

The first program module can be configured to transmit, for receipt by each of the plurality of nodes in the distributed computing network, a message that indicates the set of medical records of the first user have been made available to the account of the second user. In response to receiving the message, each respective node among the plurality of nodes in the distributed computing network can be configured to add, to the respective instance of the electronic ledger stored at the respective node, a record of a medical record management event that occurred between the account of the first user and the account of the second user based on the message.

Entries of medical record management events included in the electronic ledger can be respectively assigned to different ones of a plurality of groups of records. The groups of records can be chronologically ordered in the electronic ledger and each respective group of records can include a signature of the group of records that immediately precedes the respective group of records in the chronological ordering of the groups of records.

The signature included in each respective group of records can include a hash value of the group of records that immediately precedes the respective group of records in the chronological ordering of the groups of records.

The electronic ledger can comprise a blockchain database.

At least one of the first program module, the second program module, or the third program module can be stored on the electronic ledger, wherein executing the at least one of the first program module, the second program module, or the third program module includes accessing the at least one of the first program module, the second program module, or the third program module from the electronic ledger.

The second user can be a medical professional and the first user is a patient of the medical professional.

A given medical record management event having an entry stored in the electronic ledger can include a request to access a medical record of a user, an authorization for a participant in the distributed computing network to access a medical record of a user, a denial of authorization for a participant in the distributed computing network to access a medical record of a user, addition of a medical record of a user, update of a medical record of a user, or deletion of a medical record of a user.

At least some of the entries of medical record management events stored on the electronic ledger may be associated with program modules assigned to accounts of different users on the distributed computing network.

The set of medical records of the first user can be stored on a second computing system separate from the electronic ledger and the first program module. The first program module can store data that indicates a location of the set of medical records of the first user on the second computing system. The first program module can be arranged to make the set of medical records of the first user available to the account of the second user by providing the data that indicates the location of the set of medical records of the first user to the account of the second user.

The set of medical records of the first user can be encrypted on the second computing system. The first program module can be arranged to make the set of medical records of the first user available to the account of the second user further by providing to the account of the second user one or more decryption keys capable of decrypting the set of medical records of the first user on the second computing system.

The second computing system on which the set of medical records of the first user are stored can include a distributed filesystem that is configured to allow medical records to be shared among participants in the distributed computing network using a peer-to-peer file transfer protocol.

The system can further include executable code that is arranged to determine whether medical record management events invoked by at least one of the first program module or the second program module are valid.

The computing system can further include a third program module assigned to an account of an emergency medical professional on the distributed computing network. The third program module can be arranged to access for emergency use at least respective subsets of medical records of a plurality of users on the distributed computing network by calling respective program modules assigned to the plurality of users, wherein the respective program modules assigned to the plurality of users do not identify the account of the emergency medical professional as being authorized to access medical records of the plurality of users.

Participants in the healthcare network may be restricted from invoking medical record management events based on respective roles assigned to the participants, wherein the roles are selected from a group consisting of a government, a rights manager, a medical professional, a patient, an insurer, a pharmacist, and a hospital.

The first and second program modules can be provided in the form of first and second smart contracts, respectively.

Some implementations of the subject matter described herein can include a computer-implemented method. The method can include identifying a command from a first user to access a medical record of a patient having an account on a computing network, wherein each of a plurality of nodes of the computing network maintains a respective instance of an electronic ledger that stores information about medical record management events associated with respective user accounts among a plurality of user accounts; in response to identifying the command to access the medical record of the patient, using a first program module assigned to the first user to generate a request to access the medical record of the patient; providing the request to access the medical record of the patient to a second program module not assigned to the first user, wherein the second program module is arranged to determine whether the first user's request to access the medical record of the patient is a valid request; in response to identifying that the second program module has determined that the first user's request to access the medical record of the patient is a valid request, calling a third program module that is assigned to the patient, wherein the third smart contact is arranged to make the medical record of the patient available to the account of the first user if the first user has been authorized by the patient to access medical records of the patient; and receiving, at the account of the first user, the medical record of the patient or information usable to access the medical record of the patient.

These and other implementations can optionally include one or more of the following features.

Each respective node of the plurality of nodes of the computing network can add to the respective instance of the electronic ledger an entry that indicates information about the request to access the medical record of the patient.

The first program module and the second program module can each be stored on the respective instances of the electronic ledger maintained by each of the plurality of nodes of the computing network.

Some implementations of the subject matter described herein can include a computing system that includes one or more processors and one or more computer-readable media having instructions stored thereon that, when executed, cause performance of operations. The operations can include identifying a command from a first user to access a medical record of a patient having an account on a computing network, wherein each of a plurality of nodes of the computing network maintains a respective instance of an electronic ledger that stores information about medical record management events associated with respective user accounts among a plurality of user accounts; in response to identifying the command to access the medical record of the patient, using a first program module assigned to the first user to generate a request to access the medical record of the patient; providing the request to access the medical record of the patient to a second program module not assigned to the first user, wherein the second program module is arranged to determine whether the first user's request to access the medical record of the patient is a valid request; in response to identifying that the second program module has determined that the first user's request to access the medical record of the patient is a valid request, calling a third program module that is assigned to the patient, wherein the third smart contact is arranged to make the medical record of the patient available to the account of the first user if the first user has been authorized by the patient to access medical records of the patient; and receiving, at the account of the first user, the medical record of the patient or information usable to access the medical record of the patient.

In some implementations, the techniques described herein can, in certain instances, realize one or more of the following advantages. An electronic medical records system can be implemented that provides a publicly verifiable record of transactions related to medical records identified in the network without revealing the contents of medical records to unauthorized users. The medical records system can restrict access to medical records to only authorized users and can verify a strong link between a user's real identity and virtual identity. Additionally, the medical records system may allow medical records to be securely shared without need for a central authority and for transactions to occur among participants in the network in a trustless environment. In some implementations, the distributed medical records system can provide a comprehensive medical records platform for linking different healthcare stakeholders. For example, a physician may seamlessly add a prescription to a patient's smart contract, and the prescription may be automatically shared with a pharmacist to be filled. Once the prescription is filled, the pharmacist may send on the ledger a receipt to the patient to indicate the prescription has been filled and to notify other pharmacies that the prescription has been filled should the user attempt to double-fill the prescription. Thus, the techniques described herein may alleviate at least some problems related to incompatibilities of existing electronic medical records systems used by different healthcare organizations. The techniques described herein may also preserve the privacy and identities of users on the network and respect the sensitive nature of medical records.

Moreover, the network architecture discussed herein may provide a seamless mechanism for efficiently and securely distributing records to appropriate user. Not only are the security of the medical records improved, but the computing resources expended to distribute, access, or grant access to a medical record can be reduced by more efficiently directing medical records to appropriate users with verification mechanisms. In some implementations, rights manager mart contracts on a distributed healthcare records network can reduce the occurrences of false transaction on the network by validating network calls before they calls are fully performed. In this way, fewer invalid calls may clutter the network (reducing channel bandwidth usage) and the nodes in the network may be prevented from performing computationally expensive transactions if the call to perform the transaction is determined to be invalid by the rights manager. In some implementations, storing the medical records off of the distributed ledger (e.g., in an external filesystem) can reduce the storage requirements of individual network nodes and can obviate any need for each record to be transmitted to transmitted to network nodes for users that are not associated with the record.

DESCRIPTION OF DRAWINGS

FIG. 8 is a flowchart of an example process for accessing a medical record of a patient using a distributed ledger.

Like references and indicators among the drawings indicate like elements.

DETAILED DESCRIPTION

This document generally describes systems, methods, devices, and other techniques for managing electronic medical records in a distributed computing system. The techniques described herein can, in some cases, provide reliable and efficient access controls that protect medical records from unauthorized use, while also facilitating secure and efficient sharing of medical records among authorized users. For example, a collection of independent nodes in a computing network may each maintain a respective instance of a distributed ledger. The distributed ledger may store records of transactions that have occurred on the network, including information about medical records for a population of patients. In particular, the distributed ledger may store, among records of other transactions, a record of every attempt made to access a given medical record maintained on the network. Moreover, the network may be arranged so as to substantially prevent the possibility of information recorded on the ledger from being deleted or otherwise manipulated. Transactions can also be verified before they are added to the network to prevent fraud. In some implementations, this can be accomplished, for example, by way of cryptographic techniques and a blockchain-based ledger. Further examples and details are described in the following paragraphs with respect to the figures.

Figure 1:
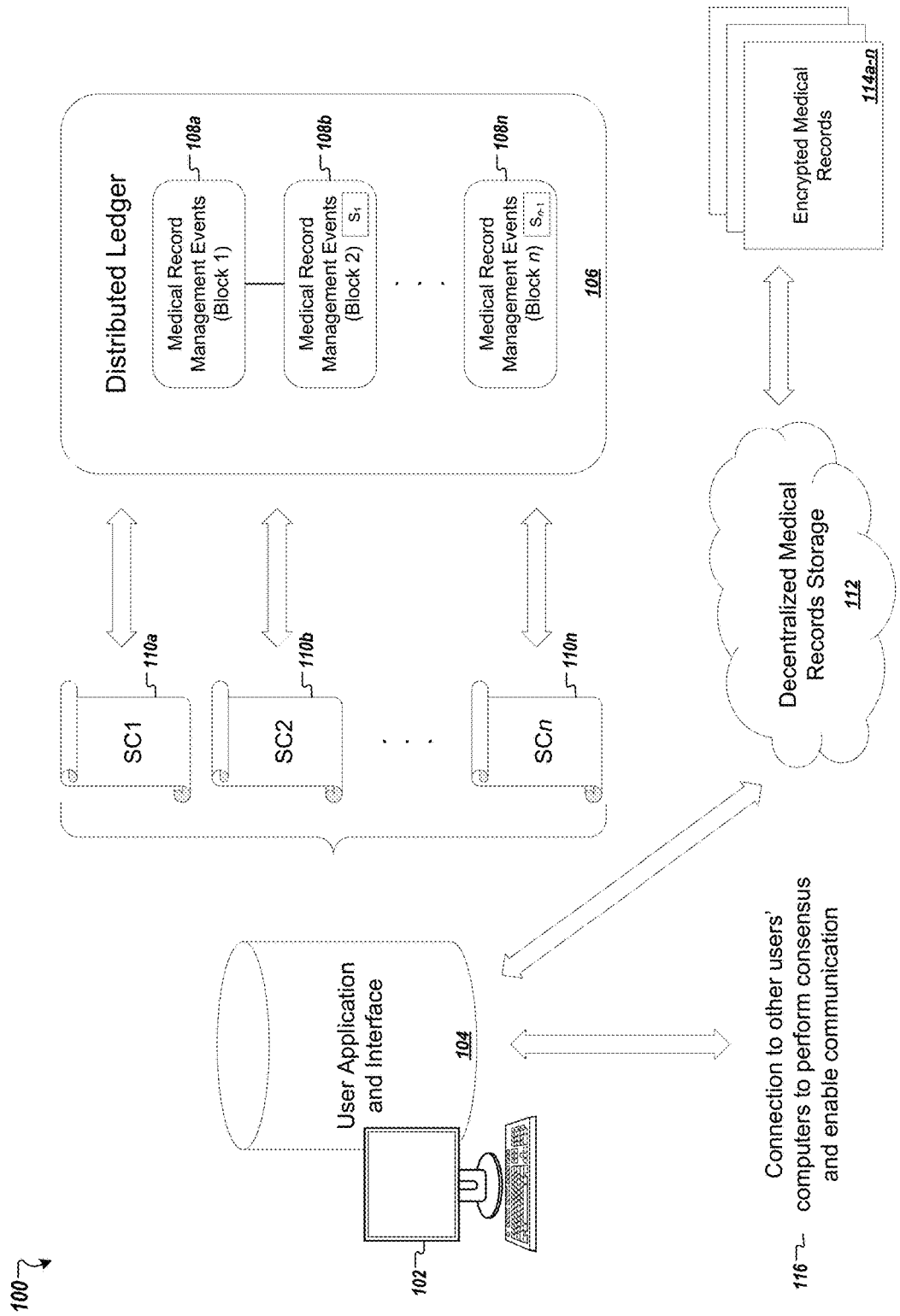
FIG. 1 is a conceptual diagram of an example computing system that operates in a decentralized computing network and uses a distributed ledger to manage medical (healthcare) records for a population of users.

FIG. 1 is a conceptual diagram of an example computing system 102 that operates in a decentralized computing network and uses a distributed ledger 106 to manage medical records for a population of users. The computer 102 may be representative of a computing node in a decentralized computing network like that shown in FIG. 2. In some implementations, the operations performed by a node in the network may be performed by a system of multiple computers, but for the purpose of discussion, the node here is represented by just a single computer 102. The computer 102 may belong to a participant in the medical records network, such as a doctor, patient, pharmacist, insurer, or hospital. The computer 102 is not limited to any particular type. For example, a desktop computer, notebook computer, a racked server, or even a mobile computing device such as a smartphone or tablet computing device may serve as a node in the computing network. The computer 102 may perform various functions, including maintaining a distributed ledger 106 and providing a terminal that allows its user to interact with the ledger 106, broadcast transactions to other nodes in the network, send and receive medical records from a storage system 112, create, review, and modify medical records if authorized, communicate with other users in the network, or perform a combination of these functions.

In some implementations, the computer 102 may be a dedicated access point that has been pre-authorized to allow a particular user to interact with the distributed ledger 106 and/or the records storage system 112. In order to ensure a strong identity of users that participate in the network, users may be restricted to accessing the network through specific access points that are physically associated with the user. These access points may have secure key management systems, for example, that store and maintain keys for the user, which can be required for the user to connect with the network. The key management system may include a collection of hardware and software mechanisms that make the system tamper-resistant such that keys cannot be intercepted, destroyed, or manipulated without proper authority. In some implementations, the key manager may be embedded (e.g., fixed) in the computer 102 such that the user must use the computer 102, or other approved devices that have similar key management systems, to access the network. In some implementations, the key management system may be a portable device that can plug into different computers to allow a user to access the network at different locations. In some implementations, in lieu of a dedicated device with a secure key management system, a user may be provided with a portable card or other device that stores one or more digital keys for a user to access the network. Computers that are capable of logging onto the network may read keys from a user's card to allow the user to authorize the user's use of a given computing station. Other forms of authentication may also be implemented that ensure a strong link between a user's real identity and virtual identity on the network.

The computer 102 may include one or more applications that provide an interface 104 for a user to interact with the network and to otherwise invoke medical record management events. The interface may include, for example, a graphical user interface or a command line interface.

In some implementations, in its role as a node in the distributed computing network, the computer 102 can store and maintain a copy of the distributed ledger 106. The ledger 106 may not be maintained by a trusted central authority, but may instead be maintained by a plurality of nodes in the computing network. Different nodes in the network may be managed and operated by different individuals, organizations, or other entities. In this way, each node in the network may separately maintain a respective copy (instance) of the ledger 106. In some implementations, the nodes in the network can act in concert to update the ledger 106 using a validation and consensus process. For example, the computer 102 may broadcast a transaction across the network so as to cause each node in the network to receive the transaction. Upon receiving the transaction, each node in the network may evaluate the validity of the transaction. If the transaction is valid, then the transaction may be added to the ledger 106. But if the transaction is invalid, the nodes may refuse to add the transaction to the ledger 106.

Valid transactions generally comply with a set of rules that are evaluated by each of the individual nodes in the network. Examples of transactions that may occur in a distributed medical records management network include calls to create smart contracts, calls to activate smart contracts, calls to add a medical record to a patient's smart contract, calls to modify a user's smart contract, calls to access a patient's medical records, calls to allow access by others to a patient's medical record, and calls to check the rights of the issuer of a transaction. A transaction may be deemed valid, for example, if the transaction includes a valid signature of the issuer, if the transaction is determined not to be a duplicate, if the parameters of the transaction are valid (e.g., includes an acceptable destination address), and if the transaction complies with any other rules set in the network.

In some implementations, the computer 102—and every other node in the network that maintains a copy of the ledger 106—may update the ledger 106 only when a consensus is reached, among at least a threshold number or portion of the nodes in the network, as to a manner in which the ledger 106 should be updated. For example, transactions may be stored in the ledger 106 in groups referred to as 'blocks.' These blocks are represented in FIG. 1 as medical record management blocks 108a-n. Together, the blocks 108a-n may include a complete record of all the transactions that have occurred in the network since its genesis. For example, the first block (108a) may include a first set of transactions that occurred in the network over a first period of time, the second block (108b) may include a second set of transactions that occurred in the network over a next (second) period of time, a third block (not shown) may include a third set of transactions that occurred in the network over a next (third) period of time, and so on.

Each node in the network that maintains a copy of the ledger 106 may maintain a queue of valid transactions that have been broadcasted over the network since a last block was formed and added to the ledger 106. In some implementations, each node may independently perform processing to determine how the queued transactions can be arranged to form a new block that satisfies certain criteria for the new blocks. For example, the nodes may each test hashes of possible block arrangements until the hash value for the block falls below a threshold hash value (e.g., a proof of work problem). This process of determining new blocks to add to the ledger 106, referred to as mining, can be computationally intensive and on average may only be completed by any node in the network after a target period of time (e.g., 2 minutes). Once a new, valid block is determined by a particular network node, that node adds the block to the ledger 106 and broadcasts information to the other nodes in the network that allow the other nodes to duplicate the block and add it to their respective copies of the ledger 106. The process can then repeat as a new queue of transactions is generated until another block is discovered to add to the ledger 106. This type of consensus procedure is sometimes referred to as a proof-of-work mechanism. However, other types of consensus procedures for updating the ledger and adding blocks may be employed in addition to or alternatively to proof-of-work mechanisms. One example of another type of consensus procedure is the practical byzantine fault tolerance (PBFT) consensus algorithm.

In some implementations, the blocks of transactions 108a-n can be chained together chronologically. That is, each time a new block is determined, that block can be appended to the end of the existing blockchain. Each block in the chain (other than the genesis block) may include a signature of one or more preceding blocks in the chain. For example, the second block 108b in FIG. 1 includes a signature of the genesis block 108a. The signature of the genesis block 108a may be a hash value of the genesis block 108a, for example. When a third block is later appended to the chain, that block may include a signature of the second block 108b. Notably, because the second block 108b includes a hash of the genesis block 108a, the signature added to the third block in the chain not only characterizes the immediately preceding block 108b, but also depends on the signature of the genesis block 108a. Thus, the signature of every new block in the chain can be at least partially influenced by every preceding block in the chain. This property can make it very difficult (and nearly impossible if the network is sufficiently large) for a nefarious actor to make unauthorized changes to blocks that have been added to the chain at an earlier time. Other nodes in the network would detect and block the unauthorized change.

In some implementations, the computer 102 may be capable of calling one or more smart contracts 110a-n to interact with the ledger 106, to initiate transactions over the distributed computing network, and to otherwise perform medical record management events. A smart contract is generally a computer program which is stored on the ledger 106 and is capable of performing operations related to medical record management.

For example, to create a smart contract, a participant on the network may write source code for the program that they wish to deploy on the network. The source code may be compiled to executable code (e.g., byte code) and packaged in a transaction that is broadcasted across the distributed computing network. As with any transaction, the respective nodes in the network may separately validate the transaction, and if valid, the transaction may be provided in a block that is permanently appended to the blockchain of the ledger 106. Thus, each node in the computing network that stores the distributed ledger may include a copy of the executable code for the smart contract. In some implementations, smart contracts may be programs that can store data, maintain state, interact with other smart contracts, interact with programs and resources off of the blockchain, or that can perform a combination of these operations. For example, a patient's smart contract may comprise code for a computer program that stores data indicating one or more medical records belonging to the patient. The patient's smart contract may include, in some instances, program code for adding records to the patient's medical history, removing records, amending records, and for granting permission to others to access the patient's records.

In some implementations, because smart contracts are stored in the distributed ledger, and copies of the ledger may be maintained at any node on the network, any node may be capable of calling and executing any smart contract. However, smart contracts may be permissioned such that certain operations in a given smart contract are performed only if it is verified that the caller of the contract (e.g., a particular node or user) has rights to execute that smart contract. In some implementations, a rights manager smart contract may maintain data that identifies users' permissions on the network and with respect to particular smart contracts or classes of smart contracts. For example, the rights manager smart contract may store data that correlates a first doctor's smart contract with a first user (a first doctor), a second doctor's smart contract with a second user (a second doctor), and a first patient's smart contract with a third user (a first patient). Each of these contracts may perform different operations depending on whether the caller of the contract has rights to call and execute the contract. Thus, if the second doctor attempts to call the smart contract assigned to the first doctor, then the requested operations (e.g., adding a medical record to the profile of a patient of the first doctor) in the called contract may be blocked because the second doctor does not have permission to use the first doctor's contract. Still, a transaction indicating the second doctor's call to the first doctor's smart contract may be broadcast across the distributed network and an entry for the transaction can be recorded in the distributed ledger. The entry may indicate, however, that the call was invalid because the second doctor lacked permission to use the called contract. In contrast, when a user that has rights to call a particular contract makes a call to that contract, the operations associated with that contract may be performed as requested and a transaction indicating a valid call and execution of the contract may be recorded on the ledger at each of the nodes in the network.

In some implementations, a smart contract assigned to a particular user can be programmed to automatically call the rights manager smart contract to verify whether the user that called the smart contract has rights to call that contract. For example, a patient that calls his personal patient's smart contract may cause the smart contract to execute. Before the patient's smart contract performs substantive operations according to the patient's request (e.g., accessing a medical record), the patient's smart contract may itself call the rights manager smart contract and pass the identity of the user that called the patient's smart contract. The rights manager smart contract may determine whether the identity of the user that called the patient's smart contract matches an identity of the patient that has been assigned the called contract. If a match is determined, then the rights manager may return an indication to the patient's smart contract that the caller of the contract is an authorized user and the patient's smart contract may then carry out the substantive operations of the contract. If a match is not determined, then the rights manager may return an indication to the patient's smart contract that the caller of the contract is not an authorized user and the patient's smart contract may not carry out the substantive operations of the contract.

In some implementations, both users (participants in the network) and smart contracts can have identities (e.g., an account) in the network. An account may have an address in the network that uniquely identifies the user or smart contract associated with the account. An account address may be used by actors in the network to send transactions to the account. For example, a user account may identify one or more smart contracts that are owned by a given user. In order for the user to create a new smart contract for himself or herself, the user may call another smart contract (e.g., a factory contract) on the network that specifically configured to create new smart contracts for users. To call the factory contract, a transaction may be sent from the user's account to the factory contract via the factory contract's address on the network. The factory contract may then be executed using values of any parameters included in the call to the contract, such as values indicating the user account to which the new contract is to be assigned and values indicating the type of contract to be created. In the process of creating a new contract for a user, the factory contract may automatically call none, one, or more other contracts on the network. The factory contract is discussed by way of example only. Generally, any contract in the network may have an address that allows the contract to be called and may be capable of calling other contracts on the network in appropriate instances.

In some implementations, when a user at the computing device 102 calls a smart contract to be executed, the call can cause each respective node in the computing network that maintains a copy of the electronic ledger 106 to separately execute the called contract and to update the ledger 106 based on any transactions that result from the calling and execution of the contract. For example, a doctor may call a first smart contract from her computer 102. The call may be broadcast to all nodes in the network, and both the computer 102 and other network nodes may separately execute the first smart contract. During execution of the first smart contract, a second smart contract may be called by the first smart contract. Each node in the computing network may then execute the second smart contract. As a result of executing the first and second smart contracts, the states of one or more user accounts, smart contracts, or both may be changed (e.g., a new medical record may be assigned to a patient or access to a medical record may be given to a third party).

Such events may be referred to as medical record management events, which can be posted to the ledger 106 after validation and consensus. In some implementations, events are recorded on the ledger as a set of one or more related transactions. For example, a single event for sharing a medical record may involve multiple transactions that are each added to the ledger 106. In some implementations, records of medical record management events may be recorded in the network even if the event is never completed. For example, an attempt to access a medical record may be recorded in the ledger even if access to the medical record is denied. The availability of such data may allow the network, in some implementations, to detect fraud or other abnormal behavior. Moreover, any effort to delete or manipulate transactions related to an event in the ledger 106 can be substantially prevented due to the decentralized consensus architecture of the system and the links between blocks in the ledger 106.

In some implementations, the computer 102 may be restricted to calling contracts that are owned by an authenticated user of the computer 102. For example, the computer 102 may be configured for use by a particular patient on the network. The patient's account may be linked to a single smart contract on the network, which, for example, may identify a set of medical records associated with the patient. When used by the particular patient, the computer 102 may be restricted, when responding to user inputs that call smart contracts for execution, to invoking execution of only the single smart contract that is linked to the patient's account. The computer 102 may restrict the patient from calling contracts that are linked to accounts of other users in the network (e.g., doctors, insurers, pharmacists) or that are otherwise not linked to the particular patient's account. In some implementations, the computer 102 may call and execute any smart contract stored on the ledger 106, but substantive operations in the called contract may be performed only if the caller is verified as having rights to use the called contract.

In some implementations, different users may be capable of registering with and authenticating themselves with a same computer 102. When a different user is logged into the computer 102, the computer 102 may allow that user to call contracts linked to his or her account but not contracts associated with other accounts. However, because some contracts may automatically call other contracts, the computer 102 may allow contracts not linked to an authorized user's account to be called by other contracts, but not to be called by the user. In some implementations, transactions may be recorded in the ledger 106 that indicate attempts by users to make unauthorized contract calls. If a call is determined to be made by a non-authorized user, the network may log the attempt but may reject the call without fully executing the called contract.

In some implementations, medical records may be stored on a system that is external to the distributed ledger 106 itself. For example, FIG. 1 shows that medical records for all or some of the patients represented in the network may be stored in a decentralized filesystem 112 off of the ledger 106. Medical records in the decentralized filesystem 112 may be physically stored at one or more of a plurality of computing nodes in a distributed network. In some implementations, all or some of the nodes in the storage network may be common to the network that maintains the ledger 106. For example, a computer 102 that belongs to a doctor may both store medical records created by the doctor for his or her patients and may also maintain an instance of the distributed ledger 106. In some implementations, all or some of the nodes in the storage network may be different from nodes in the network that maintains the ledger 106. For example, the doctor associated with the computer 102 may transmit medical records that he or she creates to one or more servers separate from the computer 102 that hosts data for the decentralized filesystem 112.

Generally, the decentralized filesystem 112 is configured to allow peer-to-peer sharing of medical records among participants in the records management system. For example, when a doctor creates a medical record that is added to a patient's smart contract, the medical record may initially be hosted by one or more computers associated with the doctor that created the record. If the patient later selects to access the record, the record may be retrieved from the doctor's computers and provided to one or more computers associated with the patient. Subsequent parties that access the record may then obtain the record from the doctor, the patient, or both. Of course, distribution of a record across the network may not occur only in response to user requests for the record at different nodes. Rather, the filesystem 112 may in some implementations automatically distribute the record to all or some of the nodes in the network before the record is requested by a given user to ensure availability of the record if a single host is offline.

The filesystem 112 may store medical records 114a-n in one or more forms. In some implementations, a distinct file (e.g., text files, images, PDFs, or other file types) may be provided for each medical record. In some implementations, the filesystem 112 may store medical records 114a-n in a database or other data structure. Each medical record may be stored as one or more related entries in the database rather than as individual files. In some implementations, medical records 114a-n on the filesystem 112 may be encrypted so that only authorized users possessing a valid decryption key can access the original record and recognize its actual content in plaintext. In some implementations, only the original owner of a file (e.g., the party that created the file) may be authorized to access the file. As access permissions are granted to other parties, a decryption key for the file may be shared with the other parties. As discussed further below, the sharing can be orchestrated by one or more smart contracts stored on the ledger 106.

Although medical records 114a-n themselves may be stored outside the ledger 106, the ledger 106 can nonetheless store data that points to the records on the external filesystem 112. In some implementations, the pointer to a record may comprise a hash value of the record referenced by the pointer. For example, when a new record is added to the system, the record may be stored on the filesystem 112 and may be indexed by a hash value computed based on the content of the record and, in some instances, further based on metadata associated with the record (e.g., a timestamp indicating the date and time the data was created, identifying information of the doctor that created the record, and/or identifying information of the patient to whom the record belongs). The hash value may be broadcast across the network in a transaction that causes the nodes in the computing network to add the hash value for the new medical record to a set of medical records identified by a smart contract of the patient to whom the record belongs. In some implementations, a medical record may be shared with other users on the network by providing the other users, or smart contracts associated with the other users, with (i) the pointer (e.g., hash value) to the medical record on the filesystem 112, (ii) information for determining a decryption key to decrypt the file, or (iii) both the pointer and the information for determining the decryption key.

Figure 2:
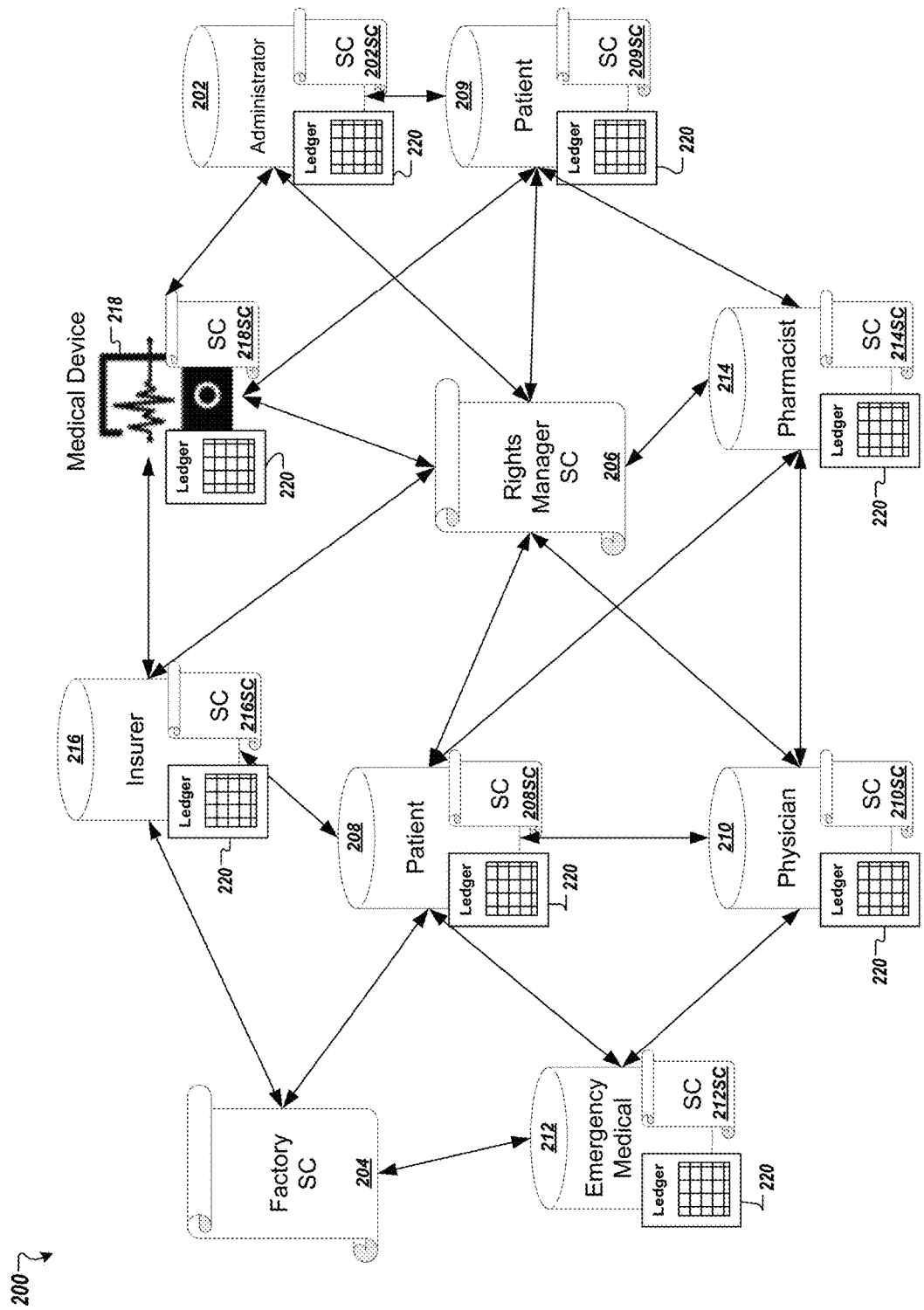
FIG. 2 is a conceptual illustration of an example decentralized computing network for managing medical records on a distributed ledger.

Referring now to FIG. 2, a conceptual illustration is shown of an example computing network 200 for managing medical records on a distributed ledger 220. The network 200 is generally a decentralized network in which records management is coordinated among potentially many distinct computers or computing systems that comprise nodes in the network. The respective computers or computing systems for all or some of the respective nodes in the network may be physically separate from each other, independently owned and operated by different entities, and/or geographically remote from each other. As such, users that participate in the network need not rely on just a single central authority to properly administer records management. Instead, records management events may be recorded on every copy of the ledger and may be transparent to all nodes in the network.

The network 200 can thus ensure a high degree of confidence in the integrity and accuracy of data recorded on the ledger 220. In some implementations, individual nodes in the network 200 can be configured in the manner of computer 102, as discussed with respect to FIG. 1.

The network 200 in FIG. 2 is a simplified view of a network that may be implemented in practice. For example, whereas only a few nodes are show in FIG. 2, the network 200 may be much larger having hundreds or thousands of nodes, for example. Additional nodes may be added even after the network 200 is originally created. Notably, FIG. 2 shows both full "validator" nodes that store and maintain respective copies of the ledger 220 in addition to virtual nodes (e.g., factory smart contract 204 and rights manager smart contract 206) that have an account and address in the network but that may not be assigned to specific users. In some implementations, a validator node may perform mining in proof-of-work consensus procedure to determine new transaction blocks to add to the ledger 220. Transactions may be sent to and from virtual nodes in the network (e.g., by calling and executing smart contracts corresponding to the virtual nodes), but the virtual nodes themselves may not be specifically associated with a particular computer or computing system that stores or maintains an instance of the distributed ledger 220. In some implementations, the network 200 may further include "thin" user nodes (not shown) that allow users to access and interact with the distributed ledger 220 but that do not independently maintain instances of the distributed ledger 220. For example, a thin node may allow a user to call a smart contract assigned to the user and to access medical records identified by the smart contract. The thin node may not, however, participate in the validation and consensus procedures necessary to coordinate updates to the ledger 220. A thin node may allow applications to be developed for mobile devices, for example, by which users can interact with the ledger 220 without requiring the devices to be always online or consuming limited computing resources.

The network 200 is generally arranged to facilitate secure maintenance, access, and sharing of medical records among appropriate parties. Users (e.g., people, organizations, or other entities) having a strong identity in the real world are represented in the figures by cylinders. For example, the network 200 may connect computers or accounts associated with a first patient 208, a second patient 209, a physician 210, a pharmacist 214, and an insurer 216. Each of these entities has a strong, real-world identity. By contrast, automated actors—generally smart contracts—are represented by scrolls in the network 200. The automated actors represent what can be done in the network and the way data may be stored in the distributed ledger 220. Some, but not all, smart contracts may be linked to a user having a strong identity in the real world and may be called by users to invoke a medical record management event such as adding a medical record to a patient's medical history or granting permissions to one or more users to access records in the patient's medical history.

In some implementations, users may be required to invoke medical record management events by smart contracts. For example, the first patient 208 may access records in his or her medical history (profile) by calling the smart contract 208SC that is linked to the first patient. Similarly, a second patient 209 may access his or her medical history by calling the smart contract 209SC, and a pharmacist 214SC may fill prescriptions specified by the pharmacist's smart contract 214SC. In some implementations, users are assigned roles on the network 200 (e.g., patient, physician, doctor, pharmacist, administrator) and smart contracts are created and correlated with the users based on the respective roles assigned to the users. Thus, if a doctor wishes to register an account on the network 200, a smart contract specific for the role of "doctor" can be created and assigned to the user, which represents the doctor's identity on the network. The type of smart contract assigned to a user may define the types of actions that the user may take on the network 200. For example, a "patient" smart contract may enable a user to access medical records of the user (but not of other users), to add authorizations for doctors or other parties to access all or some of the user's medical records, to remove authorization of parties to access all or some of the user's medical records, to send valid prescriptions to a pharmacist for filling, to pay bills to an insurer or doctor or other medical provider, and to adjust user account settings. In contrast, a "doctor" smart contract may enable a doctor to access medical records of patients under the doctor's care, to add new medical records to the respective medical histories of the doctor's patients, to send prescriptions to pharmacists on behalf of the doctor's patients, and to send invoices for medical services rendered for a patient to the patient and the patient's insurer.

In some implementations, the smart contracts assigned to users can be created based on templates that correspond to different possible roles in the network (e.g., patient, physician, doctor, pharmacist, administrator). For example, all patients in the network 200 may be assigned generally equivalent smart contracts based on a patient template and all doctors in the network 200 may be assigned generally equivalent smart contracts based on a doctor template. In some implementations, smart contracts may be at least partially customized according to the particular needs of a user. For example, insured patients may be assigned at least partially different smart contracts from non-insured patients. Similarly, a smart contract assigned to a cardiologist may at least partially differ from a smart contract assigned to an allergist or a neurologist to account for relevant differences in the types of records management events that may need to be carried out by doctors of different specialties.

As another example, the physician 210 may be the attending physician of the first patient 208 such that the physician 210 is authorized to access the entire medical history of the first patient 208 and all records associated therewith. An emergency medical provider 212 (e.g., an emergency room doctor or emergency medical technician), on the other hand, may not be authorized to access the first patient's 208 full medical history. In the event of an emergency, the medical provider 212 may nonetheless use its smart contract 212SC to access critical medical records associated with the first patient 208, such as a list of drug allergies and emergency contact information.

In some implementations, the network 200 can be created by an administrator 202. At the beginning, the network 200 can initially include an account for the administrator 202, a factory smart contract 204, and a rights manager smart contract 206. The administrator 202 may have rights in the network 200 to perform specific actions related to verifying identities of users that register in the network 200 and verifying links between users' real-world identities and network roles. For example, in order to activate a doctor's smart contract on the network 200, the doctor may need to submit to the administrator 202 evidence that demonstrates the doctor is who he or she purports to be and that the doctor is licensed to practice medicine. If the administrator 200 approves of the doctor's request to activate a type of doctor smart contract on the network 200, then the administrator 202 may call its respective smart contract 202SC to authorize activation of the doctor's smart contract.

Other types of smart contracts that may require an administrator's 202 authorization to activate include insurer smart contracts, pharmacist smart contracts, emergency medical provider smart contracts, and others. In some implementations, a patient's smart contract may be activated without pre-authorization from an administrator 202. In some implementations, multiple administrators 202 may exist on the network 200 to allow users to consult with different administrators for different requests. For example, a first administrator may be capable of activating a first type of smart contract but not a second or third type of smart contract. Conversely, a second administrator may be capable of activating the second and third types of smart contracts but not capable of activating the first type of smart contract. In some implementations, an administrator 202 may be the only network participants that possess rights to initiate creation of factory smart contracts or rights manager smart contracts.

The factory smart contract 204 is generally configured to initialize (create) and activate new smart contracts on the network 200. For example, when a new user registers with the network, the user may call the factory smart contract 204 to create a new smart contract linked to the user. In some implementations, the new smart contract may be inactive until the contract is approved (e.g., by an administrator). Upon approval, the factory 204 may activate the new smart contract for use. Before a contract is activated, it may be incapable of being used to invoke events on the network 200.

The rights manager smart contract 206 is generally configured to check the validity of transactions and calls made on the network 200 by verifying compliance with a set of rules. Transactions or calls that are deemed noncompliant may be rejected and the records management event associated with the rejected transaction or call can be cancelled for noncompliance. The rights manager 206 may check all or a portion of the transactions and calls made on the network 200. In some implementations, the rights manager 206 may check the validity of a transaction or call by verifying that all parties to the transaction or calls are authorized to be party to the transaction or call. For example, if a user issues a transaction to the network to add a new medical record to a patient's smart contract, the transaction may first be required to pass through the rights manager 206. The rights manager 206 may verify that the issuer of the transaction is a doctor or another user that has rights to add a medical record to the patient's smart contract. If the issuer has such rights, then the rights manager 206 may approve the transaction and the transaction is completed by adding the new medical record to the patient's smart contract. If the issuer does not have such rights, then the rights manager 206 may reject the transaction and the new medical record is not added to the patient's smart contract. In some implementations, a record of the rejected transaction can be recorded on the distributed ledger 220. If the issuer of the rejected transaction is seen to frequently issue rejected transactions, a fraud detector may flag the issuer as a potentially problematic actor.

In some implementations, other types of smart contracts may exist on the network 200 as well. For example, a medical device 218 may be given an identity on the network 200 and may be assigned a device smart contract 218SC. Examples of medical devices 218 include physical devices that monitor and/or assist a patient with health-related needs, such as dialysis machines, CPAP and other respiratory machines, fitness trackers, hearing aids, and the like. The smart contract 218SC may allow the medical device 218 to interact with other nodes on the network 200 and to receive and store data in a manner like other network entities that have been discussed herein. For example, a medical device 218 may be programmed to automatically generate medical reports for a patient (user of the device 218). From time to time, the device 218 may upload one or more new medical reports for the patient to a filesystem and add an indication of the new medical records to the patient's medical profile on the patient's smart contract. In some implementations, the medical device 218 may itself be re-programmed or be caused to perform other actions based on data obtained from the distributed ledger. For example, a new medical report added to the network by the medical device 218 may be analyzed by the patient's doctor, and the doctor may determine that one or more settings on the medical device 218 that affect the patient's treatment (e.g., CPAP pressure levels) require adjustment. The doctor, through his or her smart contract, may broadcast a transaction to the network addressed to the medical device's smart contract 218SC. Once the transaction is verified, the medical device's smart contract 218SC may adjust a treatment parameter for the patient accordingly. Due to the architecture of the network and transparency of transactions among nodes, the adjusted treatment can be effected efficiently and securely while minimizing risk of unauthorized users tampering with the medical device 218.

Further examples of medical record management events that may be performed on a distributed computing network using a distributed ledger like those discussed with respect to FIGS. 1 and 2 are discussed in the following paragraphs with respect to FIGS. 3-7.

Figure 3:
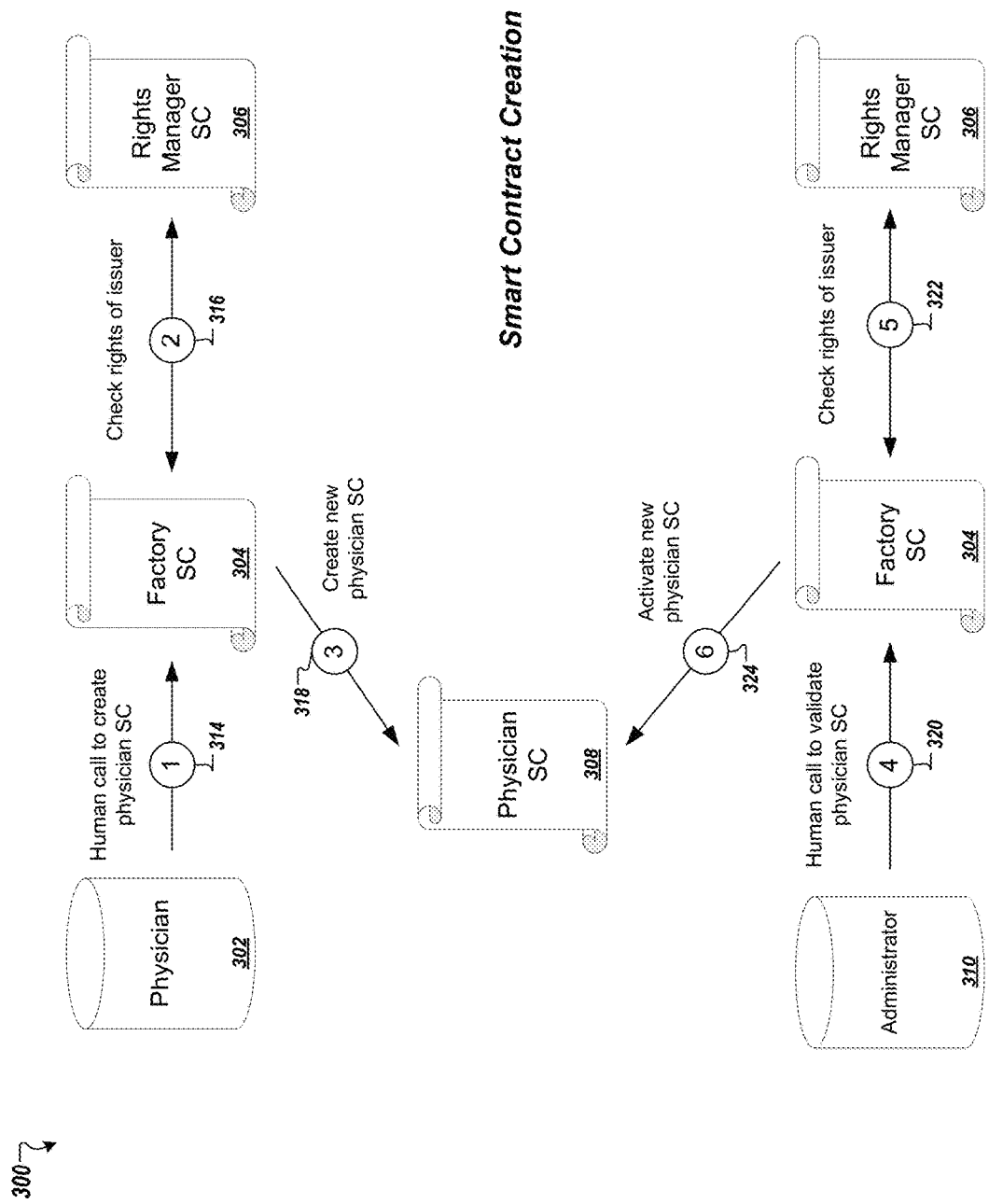
FIG. 3 is a depiction of an example process for creating a new smart contract in a distributed medical records management network.

FIG. 3 depicts an example process 300 for creating a new smart contract in a distributed medical records management system. In some implementations, the process 300 can be performed on a network that provides a distributed ledger like those discussed with respect to FIGS. 1 and 2.

At stage 1 (314), a user 302 submits a request to create a smart contract for himself or herself on the network. The user 302 may submit the request from an application on a computer that is configured to interact with the network. In some implementations, the computer from which the user 302 submits the request may be a "validator" node that stores and maintains a copy of the distributed ledger. In an open network, generally any user may download or otherwise obtain a copy of the application for interacting with the network and any user may submit a request to create a smart contract on the network. By way of example, FIG. 3 shows a physician making a call to create a physician's smart contract. However, similar processes would apply for other types of users to create new smart contracts on the network, such as contracts for patients, pharmacists, or insurers.

Based on the physician's request to create a smart contract on the network, a call is made at to the factory smart contract 304, which is a program module stored on the distributed ledger that is capable of initializing new contracts. However, before the factory contract 304 creates the new contract responsive to the request, the factory 304 first calls, at stage 2 (316) the rights manager 306 to check the validity of the request. The rights manager 306 may check, for example, that there is no reason to deny the particular physician the ability to create a new physician's smart contract. For example, if the physician 302 already has a smart contract, the call to create a second contract may be denied if the network enforces a rule that users cannot have multiple contracts or multiple contracts of the same type. If the rights manager 306 determines that the physician's 302 request is valid, the rights manager 306 can return an indication of the request's validity to the factory 304. The factory 304 then, at stage 3 (318), creates a new smart contract 308 linked to the physician 302 on the network. In some implementations, the factory 304 creates the physician's contract 308 according to a pre-defined template that indicates actions physicians can perform on the network. Like other smart contracts, the newly created physician's contract 308 may be stored on the distributed ledger so that each full (validator) node on the network maintains a copy of the contract stored on the ledger.

After the new physician's smart contract 308 is created, the physician may apply with an administrator 310 to have his or her contract 308 activated on the network. The administrator 310 may require proof from the physician 302, for example, of the physician's identity and that the physician is a licensed medical practitioner such that the physician's smart contract would be appropriate for the physician 302. If the physician's application is approved, then at stage 4 (320), the administrator 310 calls the factory smart contract 304 to activate the physician's smart contract 308. The factory smart contract 304 can then automatically call the rights manager 306 to verify that the administrator 310 has rights to invoke an activation request. Because the administrator 310 has rights to invoke activations, at stage 5 (322) the rights manager 306 authorizes the factory 304 to activate the physician's smart contract. At stage 6 (324), the factory smart contract 304 activates the physician's smart contract 308. In some implementations, activating a contract enables the contract to be called by the physician 302 and to carry out any operations requested by the physician 302 related to records management events.

In some implementations, the process 300 may be carried out by every full (validator) node on the network that maintains a copy of the distributed ledger. For example, the physician 302 may submit a call at a first computer in the network for the new contract to be created. The physician's call may be transmitted to each other node in the network to invoke performance of the process 300 at each of the other nodes. For instance, both the first computer and other computers in the network may, responsive to the physician's call, execute respective instances of the factory contract 304 and rights manager contract 306 to create respective copies of the new physician's contract 308 at each node. In some implementations, each transaction or call (e.g., each stage represented in the process 300) may be individually recorded in the distributed ledger 306, or only a subset of the transactions or calls may be recorded that, for example, represent milestones in the smart contract creation event. In some implementations, these principles can similarly apply to each of the processes 400-700 illustrated in FIGS. 4-7. That is, transactions and calls may be broadcast across the network so that each of at least a subset of nodes in the network independently performs the respective operations of the processes 400-700. All or some of the operations (e.g., transactions or calls) that are made during the processes 400-700 can be recorded in the distributed ledger. The nodes may then validate new entries to the ledger and reach consensus for adding new blocks of transactions to the ledger in a coordinated manner.

Figure 4:
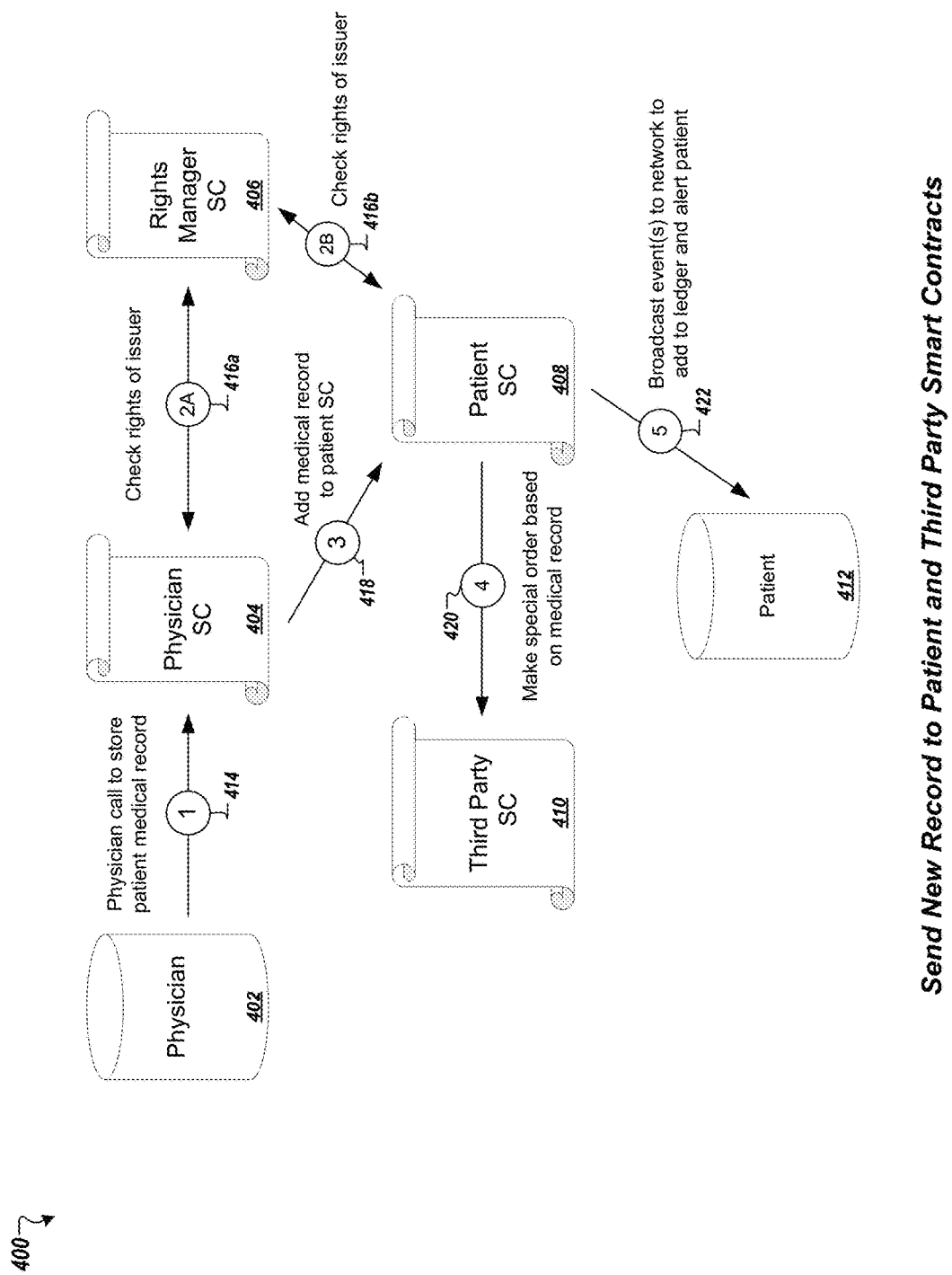
FIG. 4 depicts a flow of transactions, calls, and smart contract executions in an example process for sending medical records to a patient or other users in a distributed medical records management network.

FIG. 4 depicts a flow of transactions, calls, and smart contract executions in an example process 400 for sending medical records to a patient or other user in a distributed network. As an example, the process 400 may be performed by a physician 402 following an appointment in which the physician 402 has examined the patient 412 to diagnose an ailment. As a result of the appointment, the physician 402 may generate one or more medical records that include a diagnosis of the ailment, lab results related to the diagnostic, and a prescription that the physician 402 has written for the patient 412 for medication to treat the ailment. The physician 402 may also generate an invoice for services rendered and any other costs associated with the diagnostic. Each record generated by the physician 402, or an agent of the physician 402, can be uploaded to a storage system that makes medical records available to authorized users. Initially, the medical records may be accessible only by the physician 402 until the physician 402 delegates access to other users, such as the patient 412. In some implementations, the storage system can be a distributed filesystem for peer-to-peer sharing of medical records between authorized users. In some implementations, medical records on the filesystem can be encrypted to protect their contents from view by unauthorized users who do not possess the requisite decryption keys to view the records.

At stage 1 (414), the physician 402 calls a physician's smart contract 404, which is linked to the physician 402, to add a set of one or more medical records to the patient's medical profile. The call to the physician's contract 404 can include data that identifies the set of medical records that are to be sent to the patient. In some implementations, medical records may be identified by pointers that indicate addresses of the records on the external filesystem at which the physician 402 has uploaded the records. In some implementations, the pointer to a medical record may comprise a value of a hash of the record, which can be used by the filesystem at a later time, along with a hash table, to lookup the record when requested by an authorized user.

The call at stage 1 (414) invokes execution of the physician's contract 404. The physician's contract 404 calls, at stage 2A (416a), the rights manager contract 406 to validate the request to add medical records to the patient's medical profile. In some implementations, the rights manager 406 can check that the physician is authorized to add medical records to the medical profile of the particular patient 412. By default, actors on the network may not be able to add medical records to a patient's medical profile unless the patient specifically authorizes an actor (e.g., physician) to add records to the patient's profile. The patient's smart contract 408 may identify a list of actors that are authorized to add medical records to the patient's profile. Thus, the rights manager 406 may, at stage 2B (416b), check with the patient's smart contract 408 to determine whether the physician 402 is among the list of authorized actors to add medical records to the patient's profile. If the physician 402 is authorized, then the rights manager 406 allows the physician's smart contract 404 to send, at stage 3 (418), data for causing the patient's smart contract 408 to add the set of medical records to the patient's medical profile. In some implementations, the data conveyed from the physician's smart contract 404 to the patient's smart contract 408 includes the pointers to the set of medical records on the external filesystem. In some implementations, the data can further include one or more decryption keys for decrypting the stored medical record.

Figure 5:
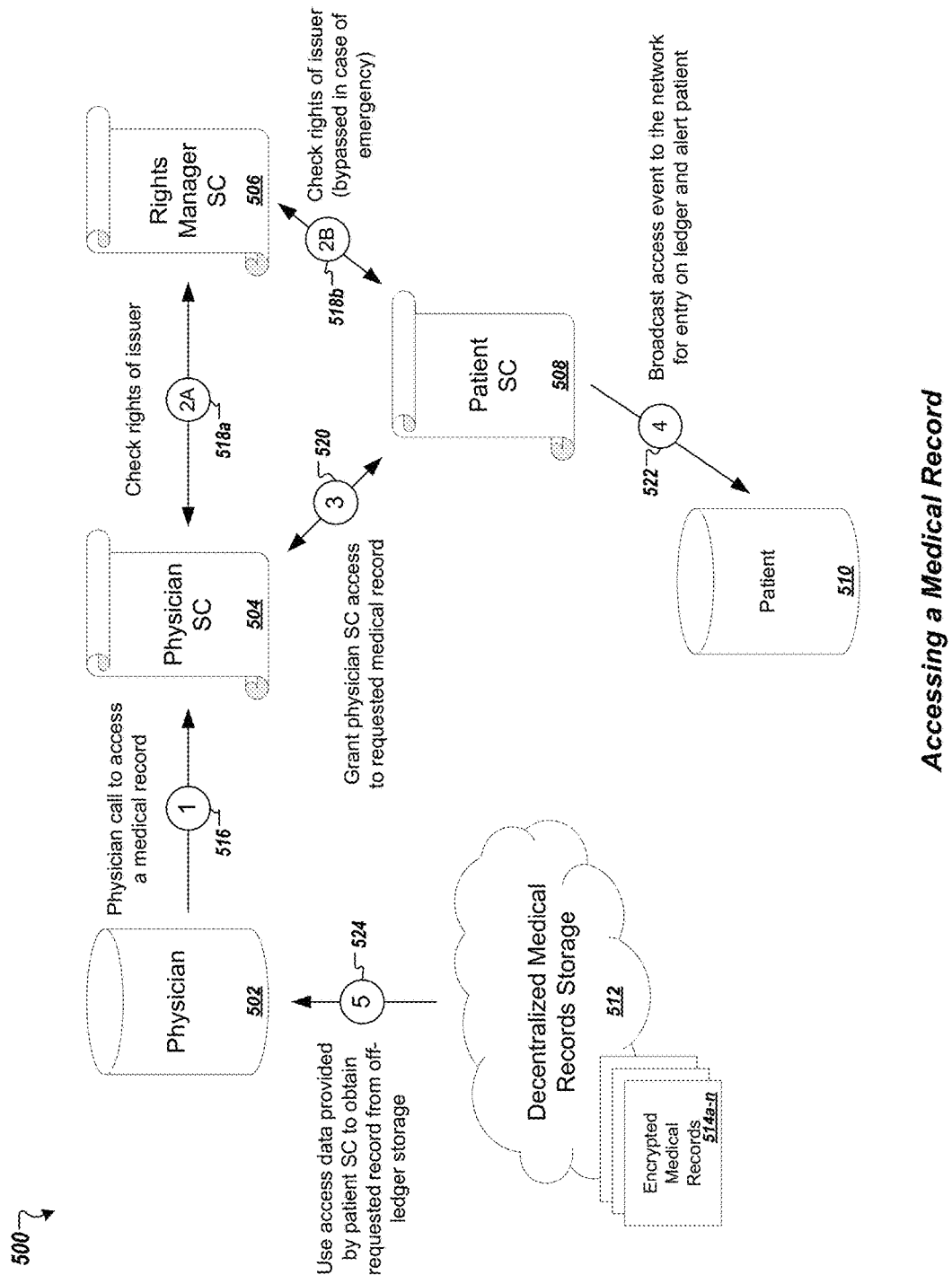
FIG. 5 depicts a flow of transactions, calls, and smart contract executions in an example process for accessing a medical record of a patient in a distributed medical records management network.

In some implementations, after the patient's smart contract 408 has added a new medical record to the medical profile of the patient 412, the contract 408 can automatically generate an alert for the patient 412, such as by sending an e-mail message or text message (e.g., SMS message) to the patient 412. The patient alert is represented in FIG. 5 at stage 5 (422), for example. In some implementations, the patient's smart contract 408 may send a new medical record to a third party either automatically or on request of the patient 412 (see stage 4 (420)). For example, the patient 412 may configure the smart contract 408 to automatically send any new prescriptions to a smart contract 410 linked to the patient's 412 preferred pharmacy. Although not expressly shown in FIG. 4, when a medical record is sent to the pharmacist's smart contract 410, the transaction may first be validated by the rights manager 406. The pharmacist linked to the third party smart contract 410 may fill the prescription and may then call the smart contract 410 to identify when the prescription has been filled. The smart contract 410 may then automatically notify the patient's smart contract 408 that the prescription 408 has been filled. Once a prescription is filled, the patient's smart contract 408 may block the prescription from being sent to other pharmacies so as to prevent patients from shopping prescriptions to multiple pharmacies to be filled multiple times.

FIG. 5 depicts a flow of transactions, calls, and smart contract executions in an example process 500 for accessing a medical record of a patient. In some implementations, access privileges to a medical record can be limited to a user that initially generated the record, such as a physician. Once a record is assigned to a patient, however, the record can be owned by the patient such that the record becomes accessible only to the patient, to users that are authorized by the patient to access the record, and to some special types of users that have special access to all or some medical records of a patient in limited circumstances (e.g., emergency medical personnel). Generally, therefore, a doctor that wishes to access a patient's medical record must be authorized by the patient to access medical records of the patient. In some implementations, the patient may grant access privileges to a doctor by calling the patient's smart contract with a command to mark the doctor as the patient's attending physician or to otherwise designate the doctor as authorized to access the patient's medical records. Data can thereafter be stored on the distributed ledger in association with the patient's smart contract to indicate that the doctor is authorized to access the patient's medical records.

In the example depicted in FIG. 5, a physician 502 holding access privileges to a patient's medical records requests to access a medical record of the patient 510. At stage 1 (516), the physician calls a physician's smart contract 504 that is linked to the physician 502 on the network. The call to the physician's smart contract 504 can include information indicating the physician's desire to access a medical record of the patient 510. At stages 2A and 2B (518a and 518b), the physician's smart contract 504 calls the rights manager 506, which validates the call to access the patient's medical record. The rights manager 506 may, for example, may confirm that the physician's smart contract 504 was properly called by the physician 502, rather than an unauthorized user that is not linked to the physician's smart contract 504. The rights manager 504 may also call the patient's smart contract 508 to verify that the physician 502 (or the physician's smart contract 504) is authorized to be sent medical records from the patient 510.

If the rights manager 506 validates the call to access the patient's medical record, then at stage 3 (520), the physician's smart contract 504 calls the patient's smart contract 508 with a request for one or more medical records in the patient's medical profile. In some implementations, the patient's smart contract 508 may check that the request has been validated by the rights manager 506, and if so, the patient's smart contract 508 provides data to the physician's smart contract 504 for accessing the requested medical records. In some implementations, the access data provided to the physician's smart contract 504 can include a pointer to the file on an external filesystem, a decryption key for decrypting the file, or both a pointer and a decryption key. In some implementations, at stage 4 (522), the patient's smart contract 508 may generate an alert for the patient 510 indicating that the patient's medical records have been shared with another party. For example, an e-mail or text message can be automatically sent to the patient. At stage 5 (524), the physician 502 use the access data provided from the patient's smart contract 508 to retrieve the requested medical records 514a-n from the external filesystem 512.

Figure 6A:
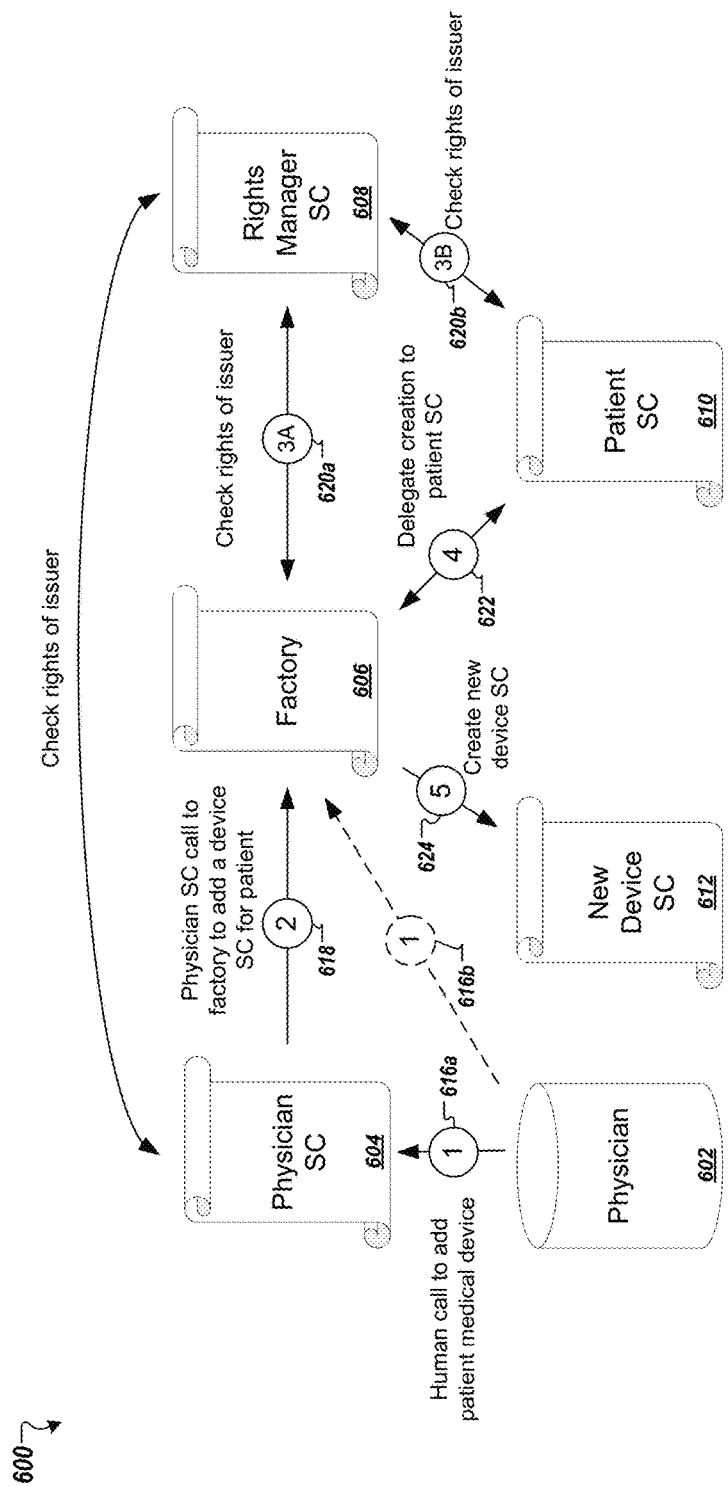
FIG. 6A depicts an example process for creating a smart contract for an automated medical device in a distributed medical records management network.
Figure 6B:
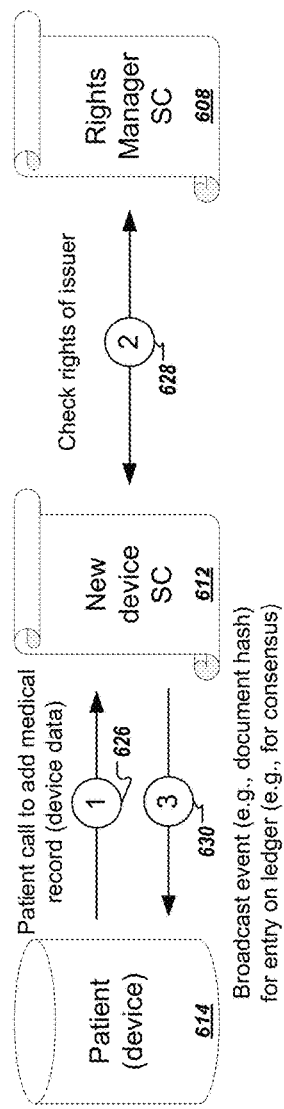
FIG. 6B depicts an example process for submitting a medical report generated by an automated medical device to a patient's medical profile in a distributed medical records management network.

FIGS. 6A and 6B depict flows of transactions, calls, and smart contract executions in an example process 600 for creating and using a smart contract representing a medical device in the network. In addition to representing human actors, the system may also allow medical devices to be represented in the network as automated actors (e.g., hearing aids, heart pumps, respiratory machines, dialysis machines). In some implementations, only doctors or other authorized healthcare providers may create have permission to create smart contracts for medical devices for a patient. In some implementations, healthcare providers may apply with an administrator for the ability to initiate creation of one or more classes of medical devices. If the administrator approves the request, then a smart contract linked to the healthcare provider can be made capable of allowing the healthcare provider to initiate creation of the requested classes of medical devices. In some implementations, a medical device smart contract is, like a patient-type smart contract, linked (assigned) to a patient so as to represent that the patient is the owner of the medical device. Once the medical device smart contract is added to the network and stored on the distributed ledger, the physical medical device represented by the contract may be capable of posting documents to the network. The documents posted by the medical device may be correlated with a virtual identity of the medical device on the network (e.g., correlated with the medical device contract), and by extension may be correlated with the patient to whom the medical device contract is linked. The medical device contract may restrict the medical device to performing certain actions on the network, such as posting medical records generated by the device and alerting the patient and/or the patient's doctors in the event of an emergency or when other abnormal events occur. For example, a continuous positive airway pressure (CPAP) machine may generate sleep respiratory reports characterizing aspects of a patient's breathing during a sleep cycle. The CPAP machine may be connected to the distributed network and may call the device's smart contract on the network to upload the report to secure storage and to add a record of the report to the patient's medical profile indicated by the patient's smart contract. The report may then be made available to the patient, the patient's doctor, or other relevant parties (e.g., insurers) that are authorized to receive the report.

Now referring to FIG. 6A, an example process is depicted for creating a new device smart contract. At stage 1 (616), a physician 602 calls his or her personal physician's smart contract 604 with a command to create a new device contract for a particular patient. In response, the physician's smart contract 604 calls, at stage 2 (618), the factory smart contract 606 to initialize and activate a new device smart contract 612. The factory 606 first checks that the physician 602 has rights to call for the creation of new device smart contracts (stages 3A and 3B (620a and 620b)). After verifying the validity of the call, the factory 606 can, in some implementations, initialize and activate a new medical device contract 612 based on the physician's call. The new device contract 612 can be linked to the patient to designate the patient as the owner of the contract. In some implementations, the factory 606 may alternatively delegate creation of the device smart contract 612 to the patient's smart contract 610 in order for the new device contract 612 to be properly linked to the patient's smart contract 610. For example, after calling the rights manager 608 to validate the request from the physician's smart contract 604, the factory 606 may call the patient's smart contract 610 with an instruction to callback the factory 606. The patient's smart contract 610 responds, at stage 4 (622), by calling the factory 606 with a command to create the new device smart contract 612. At stage 5 (624), the factory 606 creates the new device smart contract 612, which can be distributed and stored on the ledger at each node in the network.

FIG. 6B shows an example process of posting a new medical record generated by a patient's medical device to the network. In some implementations, device may automatically post records based on a set of triggering conditions (e.g., periodically or immediately following the creation of a new record). In some implementations, a patient may manually invoke an event to post a medical record from a device onto the network. Thus, as shown in FIG. 6B, at stage 1 (626), the patient or the device 614 makes a call to the new device smart contract 612 to add a new medical record to the patient's medical profile. At stage 2 (628), the device 612 checks the rights of the submitter of the request by calling the rights manager 608. Identifying information for the new medical record can then be added to the patient's smart contract and made available to the patient 614 at stage 3 (630).

Figure 7:
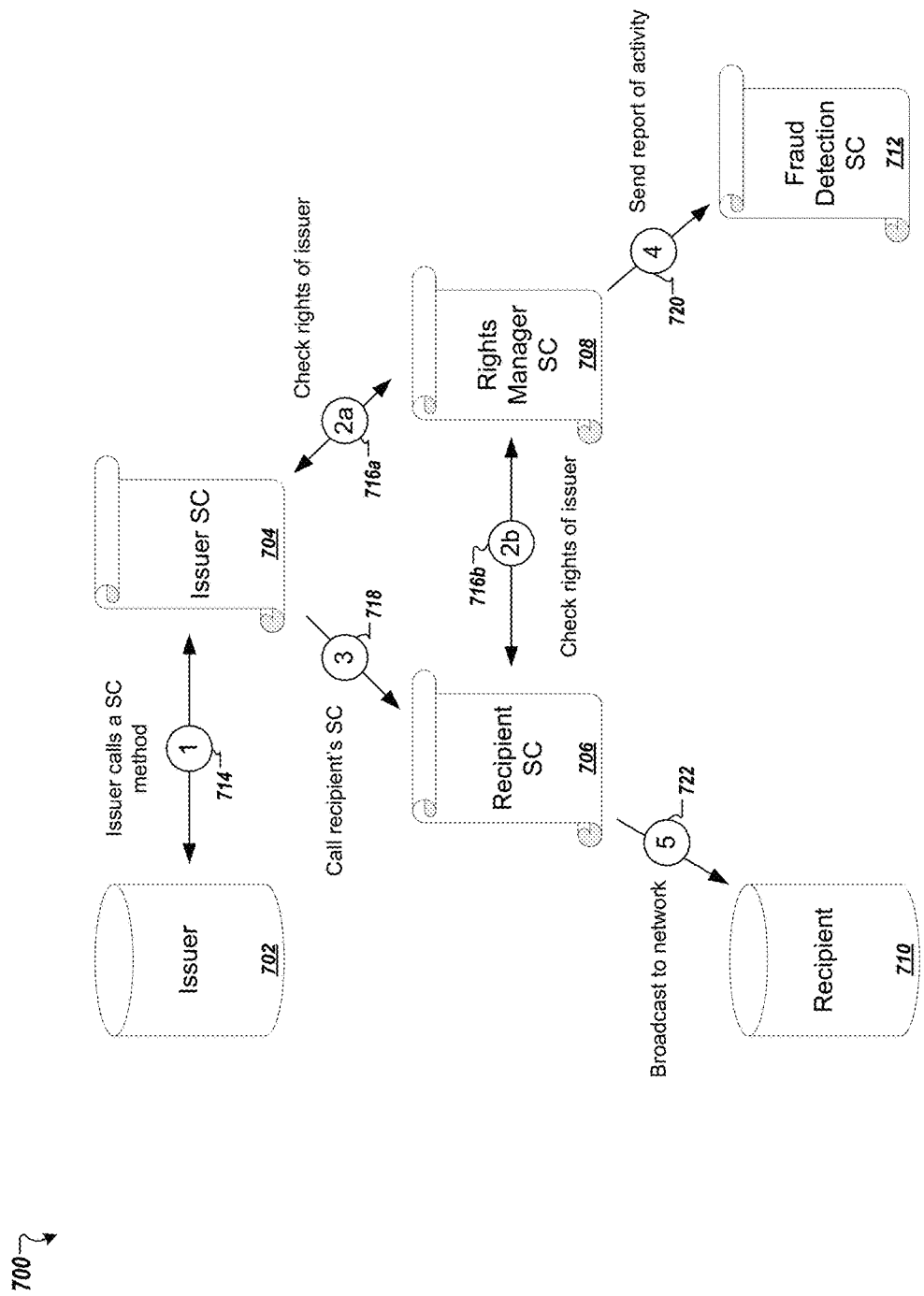
FIG. 7 depicts an example flow of transactions, calls, and smart contract executions in an example process for performing fraud detection in a distributed medical records management network.

FIG. 7 depicts a flow of transactions, calls, and smart contract executions in an example process 700 for performing fraud detection on a distributed network for records management. In some implementations, the network may include one or more smart contracts that are configured to analyze transactions that have occurred in the network over a period of time and to flag transactions that are related to potentially fraudulent activity (or otherwise abnormal activity). The architecture of the network and the distributed ledger themselves may ensure protection and constituency of data recorded in the network, but by itself may not have the capability to affirmatively detect fraud and other types of abnormal activity. To provide such capability, an administrator may create one or more fraud detection smart contracts. Because many or all transactions in the network are validated by a rights manager 708, in some implementations, the rights manager 708 may be configured to automatically call the fraud detection smart contract 712 to log transactions. The fraud detection smart contract 712 listens for and stores reports from the rights manager 708 about abnormal activity and triggers events that meet a threshold. When an event is triggered that indicates possible fraud or abnormal activity, an administrator or other user on the network may be notified to prompt further investigation. The fraud detector 712 may identify occurrences of repeated failed attempts to access one or more patients' medical records, attempts to double-fill pharmaceutical prescriptions, or suspicious doctor behavior. The process 700 can be carried out by the issuer 702, at stage 1 (714), making a call to the issuer's smart contract 704. At stage 2A (716a), the issuer's smart contract 704 calls the rights manager smart contract 708 to validate the issuer's call. The issuer's contract 704 then calls, at stage 3 (718), the recipient's smart contract 706, which in turn at stage 2B (716b) calls the rights manager contract 708. If the rights manager contract 708, for example, determines that the call was invalid, the call may be flagged in the fraud detection smart contract 712. At stage 5 (722), a result of the process 700 can then be broadcast to recipients 710 across the network.

Turning to FIG. 8, a flowchart is shown of an example process 800 for accessing a medical record of a patient using a distributed ledger. In some implementations, the process 800 may be performed by the computing system 102, described with respect to FIG. 1, which stores and maintains a copy of a distributed ledger and serves as a fully functional node in a distributed computing network. At stage 802, the computing system identifies that a first user (e.g., a doctor) of the computing system has submitted a command to access a medical record of a patient who is registered on the distributed computing network. In response to identifying the command, at stage 804 the computing system calls a first smart contract stored on the distributed ledger to obtain access for the first user to the patient's medical record. The first smart contract may be linked to the first user and may provide a portal for the first user to invoke medical record management events (e.g., accessing patient's medical records) and to otherwise interact with the ledger. At stage 806, the computing system executes the first smart contract, which in turn calls one or more other contracts on the ledger to facilitate transfer of data necessary for the first user to access the requested medical record. In some implementations, the first smart contract can call a rights manager smart contract, which at stage 808 validates the request including checking that the first user has a right to access the medical record of the patient. If the request is validated, then at stage 810 the first smart contract calls a smart contract that is linked to an account of the patient. The patient's smart contract executes in response to the call from the first user's contract and generates a transaction that is sent to the first user's contract to provide the first user with access to the requested medical record of the patient (stage 812). At stage 814, one or more transactions that occurred as a result of the requested access event can be recorded in the distributed ledger at each node in the computing network. At stage 816, the first user may then call the first user's contract to access the patient's medical record.

Figure 9:
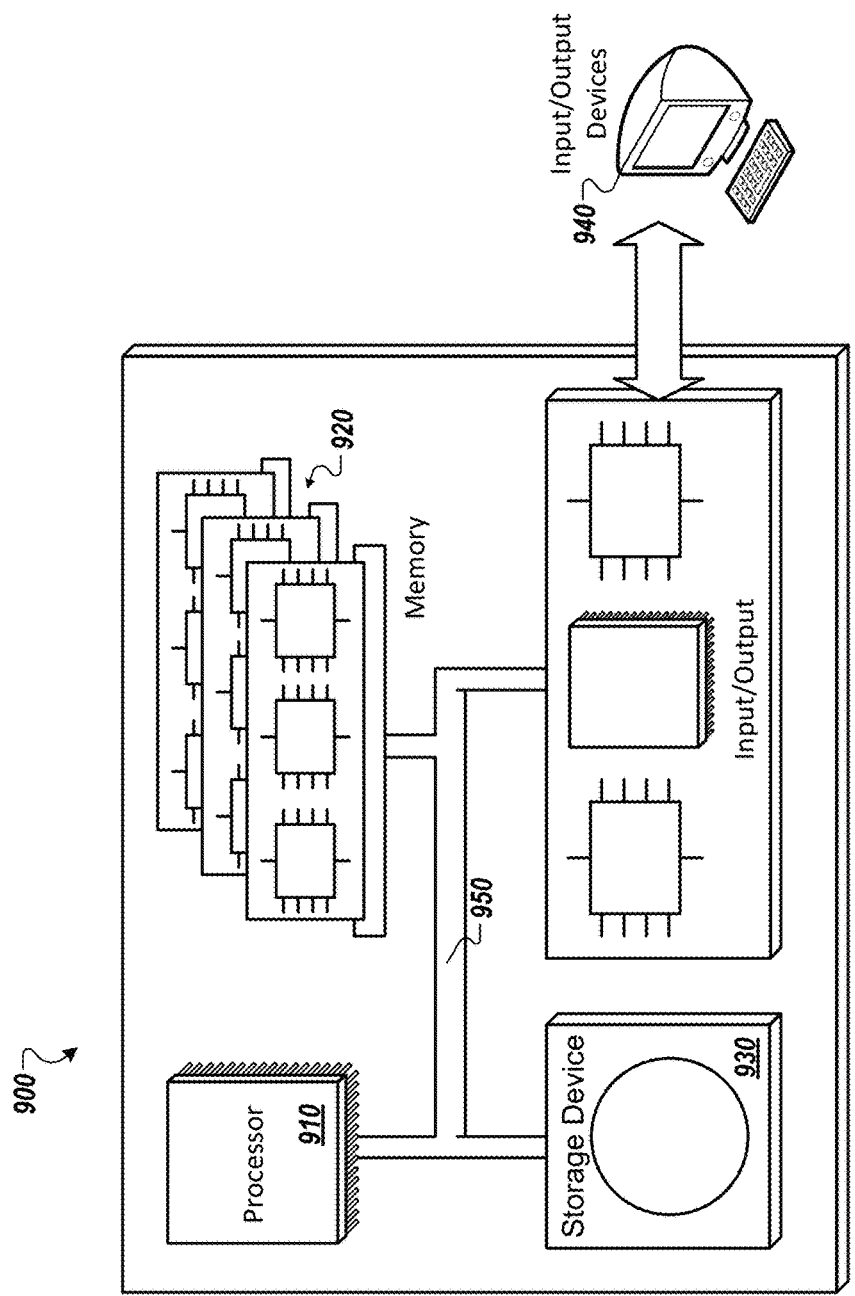
FIG. 9 depicts a schematic diagram of an example computer system that can be used in some implementations to perform the operations associated with the computer-implemented methods and other techniques described herein.

FIG. 9 is a schematic diagram of a computer system 900. The system 900 can be used to carry out the operations described in association with any of the computer-implemented methods or other techniques described previously, according to some implementations. The system 900 is intended to include various forms of digital computers, such as laptops, desktops, workstations, personal digital assistants, servers, blade servers, mainframes, and other appropriate computers. The system 900 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. The processor may be designed using any of a number of architectures. For example, the processor 910 may be a CISC (Complex Instruction Set Computers) processor, a RISC (Reduced Instruction Set Computer) processor, or a MISC (Minimal Instruction Set Computer) processor.

In one implementation, the processor 910 is a single-threaded processor. In another implementation, the processor 910 is a multi-threaded processor. The processor 910 is capable of processing instructions stored in the memory 920 or on the storage device 930 to display graphical information for a user interface on the input/output device 940.

The memory 920 stores information within the system 900. In one implementation, the memory 920 is a computer-readable medium. In one implementation, the memory 920 is a volatile memory unit. In another implementation, the memory 920 is a non-volatile memory unit.

The storage device 930 is capable of providing mass storage for the system 400. In one implementation, the storage device 930 is a computer-readable medium. In various different implementations, the storage device 930 may be a floppy disk device, a hard disk device, an optical disk device, or a tape device.

The input/output device 940 provides input/output operations for the system 400. In one implementation, the input/output device 940 includes a keyboard and/or pointing device. In another implementation, the input/output device 940 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method, comprising:
accessing an electronic ledger that stores entries of medical record management events invoked by participants in a distributed computing network, wherein respective instances of the electronic ledger are stored at each of a plurality of nodes in the distributed computing network;
storing, on the electronic ledger, a first smart contract, wherein the first smart contract is assigned to an account of a first user on the distributed computing network, the first smart contract comprising executable code programmed to identify (i) medical records of the first user and (ii) accounts of users other than the first user that are authorized to access medical records of the first user;
storing, on the electronic ledger, a second smart contract, wherein the second smart contract is assigned to an account of a second user on the distributed computing network;
calling the first smart contract with the second smart contract so as to request access on behalf of the second user to a medical record of the first user, wherein an encrypted version of the medical record of the first user is stored at a location off the electronic ledger;
based on the second smart contract calling the first smart contract to request access to the medical record of the first user, executing the first smart contract to determine whether the second user is authorized to access the medical record; and
in response to determining that the second user is authorized to access the medical record, using the first smart contract to make the medical record of the first user available to the second user by providing to the second user (i) a pointer to the encrypted version of the medical record of the first user and (ii) a decryption key capable of decrypting the encrypted version of the medical record of the first user.

2. The computer-implemented method of claim 1, wherein the first smart contract is configured to transmit, for receipt by each of the plurality of nodes in the distributed computing network, a message that indicates the medical record of the first user has been made available to the second user,
wherein in response to receiving the message, each respective node among the plurality of nodes in the distributed computing network is configured to add, to the respective instance of the electronic ledger stored at the respective node, a record of a medical record management event that occurred between the account of the first user and the account of the second user based on the message.

3. The computer-implemented method of claim 1, wherein:
the entries of medical record management events included in the electronic ledger are respectively assigned to different ones of a plurality of groups of records,
the groups of records are chronologically ordered in the electronic ledger, and
each respective group of records includes a signature of the group of records that immediately precedes the respective group of records in the chronological ordering of the groups of records.

4. The computer-implemented method of claim 3, wherein the signature included in each respective group of records comprises a hash value of the group of records that immediately precedes the respective group of records in the chronological ordering of the groups of records.

5. The computer-implemented method of claim 1, wherein the first smart contract and the second smart contract are stored on the electronic ledger, wherein executing at least one of the first smart contract or the second smart contract comprises accessing the at least one of the first smart contract or the second smart contract from the electronic ledger.

6. The computer-implemented method of claim 1, wherein the second user is a medical professional and the first user is a patient of the medical professional.

7. The computer-implemented method of claim 1, wherein a given medical record management event having an entry stored in the electronic ledger describes an event involving a request to access a medical record of a user, an authorization for a participant in the distributed computing network to access a medical record of a user, a denial of authorization for a participant in the distributed computing network to access a medical record of a user, an addition of a medical record of a user, an update of a medical record of a user, or a deletion of a medical record of a user.

8. The computer-implemented method of claim 1, wherein at least some of the entries of medical record management events stored on the electronic ledger are associated with smart contracts assigned to accounts of different users on the distributed computing network.

9. The computer-implemented method of claim 1, wherein the medical record of the first user is stored on a distributed filesystem off of the electronic ledger, wherein the distributed file system is configured to allow medical records to be shared among participants in the distributed computing network using a peer-to-peer file transfer protocol.

10. The computer-implemented method of claim 1, further comprising storing, on the electronic ledger, a third smart contract comprising executable code that is arranged to determine whether medical record management events invoked by at least one of the first smart contract or the second smart contract are valid.

11. The computer-implemented method of claim 1, further comprising storing, on the electronic ledger, a third smart contract assigned to an account of an emergency medical professional on the distributed computing network, wherein the third smart contract is arranged to access for emergency use at least respective subsets of medical records of a plurality of users on the distributed computing network by calling respective smart contracts assigned to the plurality of users, wherein the respective smart contracts assigned to the plurality of users do not identify the account of the emergency medical professional as being authorized to access medical records of the plurality of users.

12. A computing system, comprising:
one or more processors; and
one or more computer-readable devices having instructions stored thereon that, when executed by the one or more processors, cause the one or more processors to perform operations comprising:
accessing an electronic ledger that stores entries of medical record management events invoked by participants in a distributed computing network, wherein respective instances of the electronic ledger are stored at each of a plurality of nodes in the distributed computing network;

storing, on the electronic ledger, a first smart contract, wherein the first smart contract is assigned to an account of a first user on the distributed computing network, the first smart contract comprising executable code programmed to identify (i) medical records of the first user and (ii) accounts of users other than the first user that are authorized to access medical records of the first user;

storing, on the electronic ledger, a second smart contract, wherein the second smart contract is assigned to an account of a second user on the distributed computing network;

calling the first smart contract with the second smart contract so as to request access on behalf of the second user to a medical record of the first user, wherein an encrypted version of the medical record of the first user is stored at a location off the electronic ledger;

based on the second smart contract calling the first smart contract to request access to the medical record of the first user, executing the first smart contract to determine whether the second user is authorized to access the medical record; and in response to determining that the second user is authorized to access the medical record, using the first smart contract to make the medical record of the first user available to the second user by providing to the second user (i) a pointer to the encrypted version of the medical record of the first user and (ii) a decryption key capable of decrypting the encrypted version of the medical record of the first user.

13. The computing system of claim 12, wherein the first smart contract is configured to transmit, for receipt by each of the plurality of nodes in the distributed computing network, a message that indicates the medical record of the first user has been made available to the second user, wherein in response to receiving the message, each respective node among the plurality of nodes in the distributed computing network is configured to add, to the respective instance of the electronic ledger stored at the respective node, a record of a medical record management event that occurred between the account of the first user and the account of the second user based on the message.

14. The computing system of claim 12, wherein:

the entries of medical record management events included in the electronic ledger are respectively assigned to different ones of a plurality of groups of records, the groups of records are chronologically ordered in the electronic ledger, and each respective group of records includes a signature of the group of records that immediately precedes the respective group of records in the chronological ordering of the groups of records.

15. The computing system of claim 14, wherein the signature included in each respective group of records comprises a hash value of the group of records that immediately precedes the respective group of records in the chronological ordering of the groups of records.

16. The computing system of claim 12, wherein the first smart contract and the second smart contract are stored on the electronic ledger, wherein executing at least one of the first smart contract or the second smart contract comprises accessing the at least one of the first smart contract or the second smart contract from the electronic ledger.

17. The computing system of claim 12, wherein the second user is a medical professional and the first user is a patient of the medical professional.

18. The computing system of claim 12, wherein a given medical record management event having an entry stored in the electronic ledger describes an event involving a request to access a medical record of a user, an authorization for a participant in the distributed computing network to access a medical record of a user, a denial of authorization for a participant in the distributed computing network to access a medical record of a user, an addition of a medical record of a user, an update of a medical record of a user, or a deletion of a medical record of a user.

19. The computing system of claim 12, wherein at least some of the entries of medical record management events stored on the electronic ledger are associated with smart contracts assigned to accounts of different users on the distributed computing network.

20. The computing system of claim 12, wherein the medical record of the first user is stored on a distributed filesystem off of the electronic ledger, wherein the distributed file system is configured to allow medical records to be shared among participants in the distributed computing network using a peer-to-peer file transfer protocol.

21. The computing system of claim 12, wherein the operations further comprise storing, on the electronic ledger, a third smart contract comprising executable code that is arranged to determine whether medical record management events invoked by at least one of the first smart contract or the second smart contract are valid.

22. The computing system of claim 12, wherein the operations further comprise storing, on the electronic ledger, a third smart contract assigned to an account of an emergency medical professional on the distributed computing network, wherein the third smart contract is arranged to access for emergency use at least respective subsets of medical records of a plurality of users on the distributed computing network by calling respective smart contracts assigned to the plurality of users, wherein the respective smart contracts assigned to the plurality of users do not identify the account of the emergency medical professional as being authorized to access medical records of the plurality of users.

* * * * *